United States Patent [19]

Hruby et al.

[11] Patent Number: 4,518,711
[45] Date of Patent: May 21, 1985

[54] CONFORMATIONALLY CONSTRAINED CYCLIC ENKEPHALIN ANALOGS WITH DELTA RECEPTOR SPECIFICITY

[75] Inventors: Victor J. Hruby; Henry Mosberg, both of Tucson, Ariz.

[73] Assignee: Gibson-Stephens Institute, Tucson, Ariz.

[21] Appl. No.: 494,982

[22] Filed: May 16, 1983

[51] Int. Cl.³ ............... A61K 37/00; C07C 103/52
[52] U.S. Cl. .................... 514/11; 514/809; 260/112.5 E
[58] Field of Search .................. 260/112.5 E

[56] References Cited

U.S. PATENT DOCUMENTS 4,148,786  4/1979  Sarantakis ............... 260/112.5 E

OTHER PUBLICATIONS

H. I. Mosberg & P. W. Schiller, Int. J. Peptide Protein Res., 23, 462–466, (1984).
P. W. Schiller, B. Eggimann, J. DiMaio, C. Lexieux, & T. M.-D. Nguyen, Biochem. Biophys. Res. Commun., 101, 337 (1981).
P. W. Schiller & J. DiMaio, Peptides: Structure and Function, V. J. Hruby & D. H. Rich, eds., Pierce Chemical Co., Rockford, IL, pp. 269–278, (1983).
H. I. Mosberg, R. Hurst, V. J. Hruby, J. J. Galligan, T. F. Burks, K. Gee, & H. I. Yamamura, Biochem. Biophys. Res. Commun., 106, 506, (1982).
ibid., Life Sciences, 32, 2565, (1983).
H. I. Mosberg, R. Hurst, V. J. Hruby, K. Gee, H. I. Yamamura, J. J. Galligan, & T. F. Burks, Proc. Natl. Acad. Sci. USA, 80, 5871 (1983).
H. I. Mosberg, R. Hurst, V. J. Hruby, K. Gee, K. Akiyama, H. I. Yamamura, J. J. Galligan & T. F. Burks, Life Sciences, 33, Suppl. I., 447, (1983).
I. F. James & A. Goldstein, Molec. Pharmacol. 25, 337, (1984).
ibid., 35, 343, (1984).
A. D. Corbett, M. G. C. Gillan, H. W. Kosterlitz, A. T. McKnight & S. J. Paterson, Brit. J. Pharmacol. 86, 669P, (1983).
F. Porreca, H. I. Mosberg, R. Hurst, V. J. Hruby & T. F. Burks, Life Sciences, 33, Suppl. I, 457, (1983).
ibid., J. Pharmacol. Exp. Therap. 230, 341, (1984).
J. J. Galligan, H. I. Mosberg, R. Hurst, V. J. Hruby, & T. F. Burks, J. Pharmacol. Exp. Therap., 229, 641, (1984).
J. Hughes, T. W. Smith, H. W. Kosterlitz, L. A. Fothergill, B. A. Morgan & H. R. Morris "Identification of Two Related Pentapeptides from the Brain with Potent Opiate Agonist Activity", Nature, vol. 258, Dec. 18, 1975.
D. H. Coy & A. J. Kastin, "Structure–CNS Activity Studies with the Enkephalins", Pharmac. Ther., vol. 10: 657–668.
P. E. Gilbert & W. R. Martin, "The Effects of Morphine- and Nalorphine-like Drugs in the Nondependent, Morphine-Dependent and Cyclazocine-Dependent Chronic Spinal Dog", Jour. of Pharm. and Exp. Ther., vol. 198, No. 1: 66–82, 1976.
W. R. Martin, C. G. Eades, J. A. Thompson, R. E. Huppler, & P. E. Gilbert, "The Effects of Morphine- and Nalorphine-like Drugs in the Nondependent and Morphine-Dependent Chronic Spinal Dog", Journ. Pharm. and Exp. Ther., vol. 197, No. 3: 517–531; 1976.
J. A. H. Lord, A. A. Waterfield, J. Hughes & H. W. Kosterlitz, "Endogenous Opioid Peptides: Multiple Agonists and Receptors", Nature, vol. 267: 495–499, Jun. 9, 1977.

(List continued on next page.)

Primary Examiner—Delbert R. Phillips
Attorney, Agent, or Firm—Finnegan, Henderson, Farabow, Garrett & Dunner

[57] ABSTRACT

Novel compounds which are capable of binding with enhanced specificity to the delta receptor are disclosed. The compounds are a series of cyclic, conformationally constrained analogs of enkephalins which display exceptional delta receptor specificity. The compounds of the present invention are polypeptides of the formula:

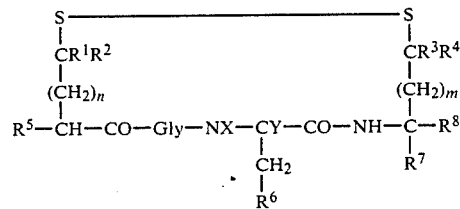

wherein $R^1$ and $R^2$, which may be the same or different, are hydrogen, methyl, or lower alkyl having 1 to 5 carbon atoms;

$R^3$ and $R^4$, which may be the same or different, are hydrogen, methyl, or lower alkyl having 1 to 5 carbon atoms, provided, however that $R^1$, $R^2$, $R^3$, and $R^4$ may not all be hydrogen when both n and m are zero;

$R^5$ is hydrogen, L-tyrosine, D-tyrosine, or L-tyrosine or D-tyrosine substituted on the $N^\alpha$-amino with 1 or 2 lower alkyl or alkenyl groups;

$R^6$ is a substituted or unsubstituted aromatic;

$R^7$ is hydrogen or methyl;

$R^8$ is carboxylate, carboxamide or amino acid residue;

X and Y are hydrogen or methyl; and, n and m, which may be the same or different, are 0 or 1.

The novel compounds include those which have either agonist or antagonist activity. The compounds may be used to induce pharmacological or therapeutic effects, including analgesia, in humans and other animals.

26 Claims, No Drawings

OTHER PUBLICATIONS

R. J. Miller & P. Cuatrecasas, "Enkephalins and Endorphins", *Vitamins and Hormones,* vol. 36: 297–375, 1978.

A. A. Waterfield, F. M. Leslie, J. A. H. Lord, N. Ling & H. W. Kosterlitz, "Opioid Activities of Fragments of Beta-Endorphin and of its Leucine 65-Analogus Comparison of the Binding Properties of Methionine- and Leucine-Enkephalin", *Euro. Jour. Pharm.,* 58: 11–18, 1978.

K. Chang & P. Cuatrecasas, "Multiple Opiate Receptors: Enkephalins and Morphine Bind to Receptors of Different Specificity", *Jour. of Biological Chem.,* vol. 254, No. 8: 2610–2617, Apr. 25, 1979.

P. W. Schiller, B. Eggimann, J. DiMaio, C. Lemieux & T. M. D. Nguyen, "Cyclic Enkaphalin Analogs Containing a Cystine Bridge", *Biochem. and Biophys. Res. Comm.,* vol. 101, No. 2: 337–343, 1981.

J. S. Morley, "Structure-Activity Relationships of Enkephalin-like Peptides", *Ann. Rev. Pharmacol. Toxicol.,* 20: 81–110, 1980.

H. W. Kosterlitz, J. A. H. Lord, S. J. Paterson & A. A. Waterfield, "Effects of Changes in the Structure of Enkephalins and of Narcotic Analgesic Drugs on Their Interactions with $\mu$- and $\delta$-Receptors", *Br. J. Pharmac.,* 68, 333–342, 1980.

B. L. Wolozin, & G. W. Pasternak, "Classification of Multiple Morphine and Enkephalin Binding Sites in the Central Nervous System", *Proc. Natl. Acad. Sci. USA,* vol. 78, No. 10: 6181–6185, Oct. 1981.

Y. Shimohigashi, T. Costa, H. Chen, & D. Rodbard, "Dimeric Tetrapeptide Enkephalins Display Extraordinary Selectivity for the $\delta$ Opiate Receptor", *Nature,* vol. 297: 333–335, 1982.

M. G. C. Gillan, H. W. Kosterlitz & S. J. Paterson, "Comparison of the Binding Characteristics of Tritiated Opiates and Opioid Peptides", *Br. J. Pharmac.,* 70: 481–490, 1980.

CONFORMATIONALLY CONSTRAINED CYCLIC ENKEPHALIN ANALOGS WITH DELTA RECEPTOR SPECIFICITY

The Government has rights in this invention pursuant to National Institutes of Health Grant No. AM-17420-08 awarded by the Department of Health and Human Services.

This invention relates to compounds that are rigid analogs of enkephalins having improved delta receptor specificity. This invention also relates to a method of inducing pharmacological manifestations associated with delta receptor agonist and antagonist activity, such as analgesia, by administering a safe and effective amount of the delta receptor specific compounds.

BACKGROUND OF THE INVENTION

Opioid analgesics are narcotics useful for treating moderate to severe pain and also useful in the treatment of diarrhea and coughing. Morphine, a plant alkaloid, is one of the most commonly known opiate drugs. Serious drawbacks associated with the plant opiates include their extreme addictiveness and their inhibition of intestinal transit. Naturally occurring opiates, known as "enkephalins," are found in the human brain, as well as in various tissues of lower animals. Naturally occurring enkephalin is a mixture of two pentapeptides and is part of a larger class of opioid peptides known as "endorphins." A considerable amount of research has been conducted in the hopes of producing a synthetic opiate which does not have the drawbacks associated with morphine.

The mechanism of the action of such opiates has only recently begun to be understood. The key to understanding that mechanism is the opioid receptor. A receptor is that entity, on a cell, which recognizes and binds a chemical substance. An opiate receptor, therefore, recognizes and binds an opiate drug. After binding with the receptor, opioid drugs may act to initiate or block various biochemical and physiological sequences. Such initiation or blockage is often referred to as transduction.

It has been found that there are several types of receptors which are affected by opioids. The major known types of opioid receptors are the mu, delta and kappa receptors. All three receptor types appear to mediate analgesia, but differ considerably in their other pharmacological effects. For example, mu receptors additionally mediate respiratory depression and inhibit gastrointestinal transit. Kappa receptors mediate sedation. While delta receptors are believed also to produce analgesia, as above described, it is believed that they do not inhibit intestinal transit in the manner associated with mu receptors. The biological activity and binding properties of opioids are directly linked to the opioid structure.

Opioid compounds structurally capable of binding at receptor sites may have a variety of biological effects, all of which are useful in attaining a variety of pharmacological and therapeutic effects. Certain opioids, known as "agonists", inhibit certain electrically stimulated outputs of neurotransmitters in tissues containing receptors, and, for example, may inhibit electrically stimulated contractions and other responses. Morphine is an agonist and acts to inhibit transmissions associated with pain and gastrointestinal tract contractions. It is also known that other substances, known as "antagonists", prevent the action of agonists by binding to the receptor without inhibiting electrically stimulated outputs in the manner associated with agonists. Naloxone is an antagonist and acts to prevent an agonist from binding at the receptor. Additionally, some substances act as either partial agonists or partial antagonists.

Naturally occurring opioid analgesics, known as endorphins, particularly enkephalins, have been extensively studied. The research began with the isolation of naturally occurring enkephalin, which is a mixture of methionine enkephalin ($H_2N$-Tyr-Gly-Gly-Phe-Met-OH) and leucine enkephalin ($H_2N$-Tyr-Gly-Gly-Phe-Leu-OH). Subsequent to the isolation of naturally occurring enkephalin, synthetic enkephalins were produced which displayed the full spectrum of enkephalin-like opioid effects.

Before proceeding further, it is necessary to explain briefly the terminology used to describe polypeptides. Peptides are identified by amino acid sequence using established abbreviations. For example, as used herein, "Gly" stands for glycine, "Leu" stands for leucine, "Tyr" stands for tyrosine, "Pen" stands for penicillamine, "Cys" stands for cysteine, "Phe" stands for phenylalanine, "Thr" stands for threonine and "Met" stands for methionine. Polypeptide derivatives in which one or more of the amino acids has been replaced by another amino acid are often described by reference to the basic compound and the position and nature of the substitution. The position of substitution is usually identified by reference to the number of the amino acid in the sequence starting with the amino acid at the amino terminus of the peptide chain. For example, $H_2N$-Tyr-Gly-Gly-Phe-Pen-OH is written as ([$Pen^5$]-enkephalin) signifying that penicillamine has been substituted for the leucine or methionine normally forming the fifth amino acid from the amino terminus in enkephalin. Additionally, amino acids may exist as stereoisomers in both L and D configurations.

The large scale use of synthetic enkephalins has been impractical due to various difficulties. One of the difficulties associated with enkephalins is that they are extremely unstable and their half-lives in the blood are extremely short. Secondly, enkephalin-like peptides are known not to cross the blood brain barrier easily. They are, however, known to cross the placental barrier and cannot, therefore, be used as analgesics during pregnancy and in childbirth without affecting the unborn child.

Attempts at solving these problems focused on altering the structure of the enkephalin molecule. Alterations in the enkephalin structure produce differing pharmacological effects. Each enkephalin analog has fairly selective effects on different systems. Specifically, it has been found that different enkephalin analogs bind to different opioid receptors. However, it has been difficult to study the role of each receptor type or to induce selectively the pharmacological and therapeutic effects associated with each receptor type because the enkephalin analogs, to date, have not had a high degree of selectivity for a single-receptor type.

Recently, it has been shown that a certain enkephalin analog is highly specific to the mu receptor. See Handa, B. K., Lane, A. C., Lord, J. A. H., Morgan, B. A., Rance, M. J., and Smith, C. F. C., *Eur. J. Pharmacol.* 70: 531–540 (1981); Kosterlitz, H. W., and Paterson, S. J., *Br. J. Pharmacol.* 77: 461–468 (1982); and, Gillan, M. G. C., and Kosterlitz, H. W., *Br. J. Pharmacol.* 73:299P (1981), all of which are specifically incorporated herein by reference. Receptor specificity has also been achieved by conformationally constraining the enkephalin peptides. Examples of such constraints include alpha or N-methylation of the peptide backbone or cyclization.

U.S. Pat. No. 4,148,786 to Sarantakis, which is specifically incorporated herein by reference, discloses a cyclic polypeptide having the following formula:

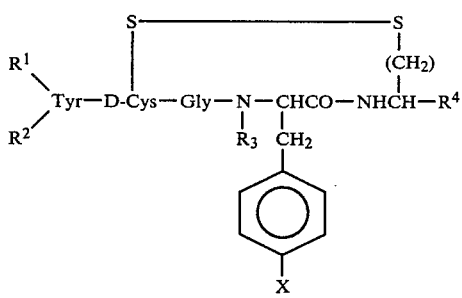

in which
R[1] is hydrogen, lower alkyl, allyl, 2-isopentenyl, 3-isopentenyl, cyclopropylmethyl, cyclobutylmethyl, phenethyl or arginyl;
R2 is hydrogen or lower alkyl;
R3 is hydrogen or lower alkyl;
R4 is hydrogen, hydroxymethyl, carbo(lower)alkoxy, carbamyl or carboxy; and,
X is hydrogen, chloro, fluoro, bromo or iodo, the linear precursors thereof or a pharmaceutically acceptable salt thereof.

The compounds disclosed by Sarantakis are said to exert an analgesic effect in warm-blooded animals when peripherally administered. However, the Sarantakis compounds are not disclosed as specific to any receptor type. Until now, few enkephalin analogs have been developed which react specifically with the delta receptor.

SUMMARY OF THE INVENTION

The present invention provides novel compounds which are capable of binding with enhanced specificity to the delta receptor (hereinafter sometimes referred to as "delta receptor specificity"). The compounds are a series of cyclic, conformationally restricted analogs of enkephalins which display exceptional delta receptor specificity. The novel compounds include those which function either as agonists or antagonists and may be used to induce pharmacological or therapeutic effects corresponding to agonist or antagonist activity in humans and other animals. A particularly preferred group of compounds are delta receptor agonists and may be used to induce analgesia in humans and lower animals without significant involvement of mu receptors and their associated side effects. Those compounds within the scope of the present invention which function as delta receptor antagonists may be used to block the action of delta receptor agonists prepared in accordance with the present invention when necessary or desirable or may be used to induce other pharmacological and therapeutic effects of opioid antagonists, such as in treatment of Alzheimer's Disease.

In accordance with the present invention, there are provided polypeptides of the formula:

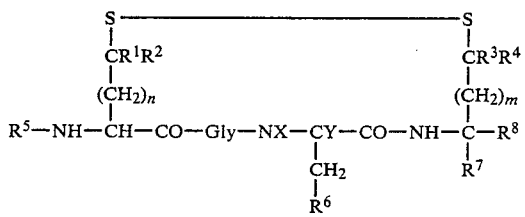

wherein
R[1] and R[2], which may be the same or different, are hydrogen, methyl, or lower alkyl having one to five carbon atoms;
R[3] and R[4], which may be the same or different, are hydrogen, methyl, or lower alkyl having one to five carbon atoms, provided, however, that R[1], R[2], R[3], and R[4] may not all be hydrogen when both n and m are zero;
R[5] is hydrogen, L-tyrosine, D-tyrosine, or L-tyrosine or D-tyrosine substituted on the $N_\alpha$-amino with 1 or 2 lower alkyl, or alkenyl groups;
R[6] is a substituted or unsubstituted aromatic radical;
R[7] is hydrogen or methyl;
R[8] is carboxylate, carboxamide or amino acid residue;
X and Y are hydrogen or methyl; and,
n and m, which may be the same or different, are 0 or 1.

All amino acid residues, except glycine, are the L configuration except for those residues in the 2 and 5 positions, and those residues, if any, in R[5] and R[8], which may be either the L or D configuration.

The compounds include both agonists and antagonists specific for the delta receptor.

The present invention is also for a process for inducing analgesia in humans and lower animals by administering a safe and effective amount of an opioid receptor agonist with delta receptor specificity as above described.

A preferred group of compounds within the present invention are delta receptor specific agonists having analgesic properties of the formula:

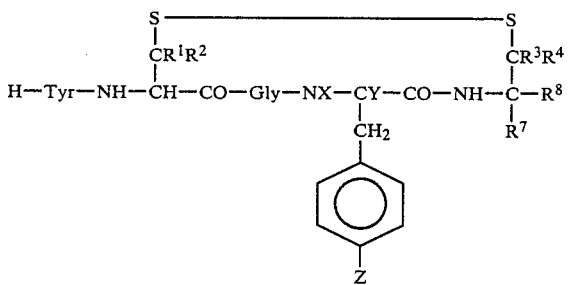

where:
R[1] and R[2], which may be the same or different, are hydrogen, methyl, or lower alkyl having one to five carbon atoms;
R[3] and R[4], which may be the same or different, are hydrogen, methyl, or lower alkyl having one to five carbon atoms, provided, however, that R[1], R[2], R[3], and R[4] may not all be hydrogen;
R[7] is hydrogen or methyl;
R[8] is carboxylate, carboxamide, or amino acid residue;
X and Y are hydrogen or methyl; and, Z is hydrogen, nitro, fluoro, or amino.
Particularly preferred compounds include

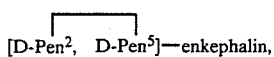
[D-Pen², D-Pen⁵]—enkephalin,

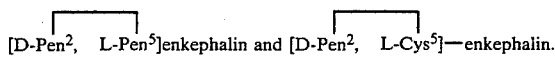
[D-Pen², L-Pen⁵]enkephalin and [D-Pen², L-Cys⁵]—enkephalin.

The compounds which are agonists may be useful as analgesics without producing the undesirable side effects associated with previously known opioids. It is believed that the agonists of the present invention are useful in pregnancy and child birth because they will not cross the placental barrier, and therefore, they will not harm the unborn child. The antagonist compounds may also be useful in the treatment of schizophrenia, Alzheimer's disease, as well as in the treatment of respiratory and cardiovascular functions.

Additional objects and advantages of the invention will be set forth in part in the description which follows, and in part will be obvious from the description, or may be learned from the practice of the invention. The objects and advantages may be realized and attained by means of the instrumentalities and combinations particularly pointed out in the appended claims.

DESCRIPTION OF THE PREFERRED EMBODIMENTS

Reference will now be made in detail to the presently preferred embodiments of the invention, which together with the following examples, serve to explain the principles of the invention.

As noted above, the present invention relates to polypeptides of the formula:

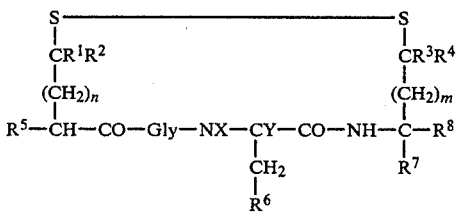

wherein
- $R^1$ and $R^2$, which may be the same or different, are hydrogen, methyl, or lower alkyl groups having one to five carbon atoms;
- $R^3$ and $R^4$, which may be the same or different, are hydrogen, methyl, or lower alkyl groups having one to five carbon atoms, provided, however, that $R^1$, $R^2$, $R^3$, and $R^4$ may not all be hydrogen when both n and m are zero;
- $R^5$ is hydrogen, L-tyrosine, D-tyrosine, or L-tyrosine or D-tyrosine substituted on the $N^\alpha$-amino with 1 or 2 lower alkyl or alkenyl groups;
- $R^6$ is a substituted or unsubstituted aromatic radical;
- $R^7$ is hydrogen or methyl;
- $R^8$ is carboxylate, carboxamide, or amino acid residue;
- X and Y are hydrogen or methyl; and
- n and m, which may be the same or different, are 0 or 1.

As noted above, a preferred group of compounds within the present invention are delta receptor specific agonists having analgesic properties of the formula:

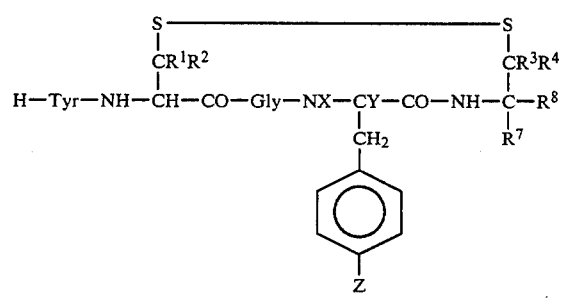

where:
- $R^1$ and $R^2$, which may be the same or different, are hydrogen, methyl, or lower alkyl having one to five carbon atoms;
- $R^3$ and $R^4$, which may be the same or different, are hydrogen, methyl, or lower alkyl having one to five carbon atoms, provided, however, that $R^1$, $R^2$, $R^3$, and $R^4$ may not all be hydrogen;
- $R^7$ is hydrogen or methyl;
- $R^8$ is carboxylate, carboxamide, or amino acid residue;
- X and Y are hydrogen or methyl; and
- Z is hydrogen, nitro, fluoro, or amino.

Particularly preferred compounds include

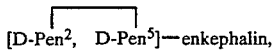
[D-Pen², D-Pen⁵]—enkephalin,

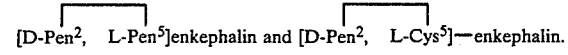
[D-Pen², L-Pen⁵]enkephalin and [D-Pen², L-Cys⁵]—enkephalin.

Specifically, the polypeptides of the present invention are cyclicized opioid compounds having greatly improved specificity for the delta opioid receptor. This increased specificity is believed to be due to the increased structural rigidity of the claimed compounds. The structural rigidity appears to stabilize the three-dimensional conformation required for activity at the delta opioid receptor, but appears to exclude the optimal conformation required for activity at the mu receptor. In a preferred group it is believed that particularly increased specificity is attributed to the presence of geminal dialkyl substituents on the amino-acid ring and, in a particularly preferred embodiment, to the presence of $\beta,\beta$-dialkyl substituents in the sulfur-containing residues at positions 2 and/or 5 of the peptide.

Such geminal dialkyl groups, combined with the S-S bridge, produce enkephalin analogs which are conformationally stable. Thus, these compounds possess the three dimensional conformation required for activity at the delta receptor and at the same time exclude the optimal conformation required for activity at the mu receptor.

For example, increased rigidity and thus increased delta receptor specificity can be conferred on the peptides disclosed by Sarantakis if the half-cysteine in the 2 position is replaced by half-penicillamine ($\beta,\beta$-dimethyl half-cysteine), preferably the D-isomer. The half-penicillamine enkephalin analog can have as much as a six hundred fold increased activity in delta receptor specific assays, compared to activity in mu receptor specific assays. The geminal dialkyl substituted compounds of the present invention also display increased delta receptor specificity in rat brain binding assays.

A unique feature of some of the preferred enkephalin analogs of the present invention is the incorporation of a half-penicillamine amino acid residue into the two and/or five position of the enkaphalin. Penicillamine is beta,beta-dimethyl-cysteine. A preferred polypeptide showing greatly increased delta receptor specificity is $$[\text{D-Pen}^2,\ \text{D-Pen}^5]\text{enkephalin}$$

and has the following formula:

$$\begin{array}{c} S \longrightarrow\!\!\longrightarrow\!\!\longrightarrow\!\!\longrightarrow\!\!\longrightarrow S \\ | \qquad\qquad\qquad\qquad | \\ C(CH_3)_2 \qquad\qquad\quad C(CH_3)_2 \\ | \qquad\qquad\qquad\qquad | \\ H-Tyr-NH-CH-CO-Gly-NH-CH-CO-NH-C-COOH \\ \qquad\qquad\qquad\qquad | \qquad\quad | \\ \qquad\qquad\qquad\qquad CH_2 \qquad\quad H \\ \qquad\qquad\qquad\qquad | \\ \qquad\qquad\qquad\quad \text{Ph} \end{array}$$

Other compounds displaying exceptional delta receptor specificity are $$[\text{D-Pen}^2,\ \text{L-Cys}^5]\text{enkephalin}$$

($R^1=R^2=CH_3$; $R^3=R^4=H$; $R^7=H$; $R^5=Tyr$; $R^6=$phenyl; $R^8=COOH$; $X=Y=H$; and $m=n=0$) and $$[\text{D-Pen}^2,\ \text{L-Pen}^5]\text{enkephalin}$$

($R^1=R^2=R^3=R^4=CH_3$; $R^5=Tyr$; $R^6=$phenyl; $R^7=H$; $R^8=COOH$; $X=Y=H$; and $m=n=0$). All compounds share the common feature of having at least one pair of geminal dialkyl groups in the ring. These dialkyl groups impose a particularly high degree of conformational restriction and steric hindrance resulting in particularly high delta receptor specificity. It is also believed that unfavorable steric and/or polar-nonpolar interactions between the $\beta,\beta$-dialkyl groups and the mu receptor binding site contributes to the observed delta receptor specificity. By altering the various amino acids, differing pharmacological properties are obtained.

An agonist will inhibit an electrically stimulated contraction in smooth muscle and an antagonist will reverse the inhibition caused by an agonist. Whether a particular compound of the present invention is an agonist, partial agonist, antagonist or partial antagonist can be determined by routine experimentation by those skilled in light of the teachings contained herein. However, the compounds of the present invention are believed to share the property of having enhanced specificity for the delta receptor.

In a preferred compound, $R^5$ is L-tyrosine. As previously stated, $R^5$ may be other substituents. For example, $R_5$ may be D-tyrosine or H as well. It is also possible to change the length, size and steric properties of the polypeptide by substituting allyl groups, alkenes or alkanes on the $N^\alpha$-amino group of the Tyrosine in the $R^5$ position. Each of these modifications will produce various biological effects which can be readily determined by assays known in the prior art through the exercise of routine skill in light of the teachings contained herein.

Modifications in ring size will also produce varying pharmacological and biological effects. For example, it is possible to substitute D- or L-homocysteine for the amino acids in either the two or five position, for example, $$[\text{D-homo-Cys}^2,\ \text{L-Pen}^5]-\text{enkephalin}$$

derivatives would have the following formula:

$$\begin{array}{c} S \longrightarrow\!\!\longrightarrow\!\!\longrightarrow\!\!\longrightarrow\!\!\longrightarrow S \\ | \qquad\qquad\qquad\qquad | \\ CH_2 \qquad\qquad\quad C(CH_3)_2 \\ | \qquad\qquad\qquad\qquad | \\ CH_2 \qquad\qquad\qquad\quad | \\ | \qquad\qquad\qquad\qquad | \\ R^5-NH-CH-CO-Gly-NX-CY-CO-NH-C-R^8 \\ \qquad\qquad\qquad\qquad | \qquad\quad | \\ \qquad\qquad\qquad\qquad CH_2 \qquad\quad R^7 \\ \qquad\qquad\qquad\qquad | \\ \qquad\qquad\qquad\qquad R^6 \end{array}$$

Similarly, substituting L-homocysteine for pencillamine, or cysteine in the five position would produce:

$$[\text{D-Pen}^2,\ \text{L-homo-Cys}^5]\text{enkephalin}$$

derivatives.

Another modification includes the addition of another amino acid in the $R^8$ position. Examples include derivatives of $$[\text{D-Cys}^2,\ \text{Pen}^5,\ \text{amino acid}^6]\text{enkephalin}$$

derivatives and more specifically $$[\text{D-Cys}^2,\ \text{Pen}^5,\ \text{Thr}^6]-,\ [\text{D-Pen}^2,\ \text{Pen}^5,\ \text{Thr}^6]-,$$

$$[\text{D-Pen}^2,\ \text{Cys}^5,\ \text{Thr}^6]-\text{enkephalins}.$$

All of these compounds behave as either agonists, partial agonists, antagonists, or partial antagonists having enhanced specificity for the delta receptor as above described.

In the fourth position, both Y and $R^6$ can be varied as above described. $R^6$ may be an aromatic radical, preferably p-nitro-phenyl, p-amino-phenyl, p-fluoro-phenyl, 1-naphthyl or 2-naphthyl.

$R^8$ can be varied by either adding an additional amino acid, thus increasing the peptide chain, or by being a carboxylate or carboxamide. If $R^8$ is a carboxylate, compounds of the present invention may be referred to as modified enkephalins. If $R^8$ is an amide, compounds of the present invention may be referred to as modified enkephalinamides. See generally, Mosberg, H. I., Hurst, R., Hruby, V. J., Galligan, J. J., Burks, T. F., Gee, K., and Yamamura, H. I., *Biochem. Biophys. Res. Comm.*, 106, 506–512 (1982), which is herein specifically incorporated by reference.

The compounds of the present invention were tested for their relative activities in the guinea pig ileum (hereinafter referred to as GPI) and in the mouse vas deferens (hereinafter referred to as MVD) assay systems, as well as for their binding properties in rat-brain receptors in competition with tritiated naloxone (hereinafter sometimes referred to as "[$^3$H]NAL" and [$^3$H][D-Ala$^2$, D-Leu$^5$]enkephalin (hereinafter sometimes referred to as "[$^3$H]DADLE"). It is generally agreed that the MVD preparation contains largely delta receptors and that the GPI preparation contains largely mu receptors. These assays tested the degree of electrically stimulated contractions in the MVD and GPI tissues. Compounds of the present invention showed a higher activity in the MVD assay than in the GPI assay, thereby confirming their enhanced specificity for the delta receptor. All agonists tested inhibited the contractions. The inhibitions of contractions were reversible by naloxone, the prototype antagonist, and are also believed to be reversible by compounds of the present invention which display antagonist activity. See generally: Kosterlitz, H. W., Lydon, R. J., and Watt, A. J., *Br. J. Pharmacol.* 39, 398–413 (1970), and Hughes, J., Kosterlitz, H. W., and Leslie, F. M., *Br. J. Pharmacol.* 53, 371–381 (1975), which are herein specifically incorporated by reference.

Table I illustrates the delta receptor specificity of some of the compounds of the present invention. As shown in Table 1, [D-Pen$^2$, D-Pen$^5$]enkephalin shows a 3,100 fold increase in delta receptor selectivity. Table II illustrates the increased delta receptor specificity of some of the compounds of the present invention in rat-brain binding assays. Specifically, the enkephalin analogs of the present invention are more effective in displacing [$^3$H][D-Ala$^2$, D-Leu$^5$]enkephalin, a ligand specific for delta receptors, than in displacing [$^3$H]NAL, a ligand specific for mu receptors.

TABLE I

Cyclic Enkephalin Analogs - Guinea Pig Ileum and Mouse vas Deferens Assays

| Analog | IC$_{50}$(nM) GPI | IC$_{50}$(nM) MVD | IC$_{50}$(GPI)/ IC$_{50}$(MVD) |
|---|---|---|---|
| [D-Pen$^2$, L-Cys$^5$] Enkephalinamide | 118 ± 19 | 3.6 ± 0.67 | 32.4 |
| [D-Pen$^2$, D-Cys$^5$] Enkephalinamide | 117 ± 21 | 16.8 ± 3.1 | 6.9 |
| [D-Pen$^2$, L-Cys$^5$] Enkephalin | 213 ± 63 | 0.32 ± 0.03 | 666 |
| [D-Pen$^2$, D-Cys$^5$] Enkephalin | 1350 ± 340 | 6.27 ± 1.2 | 215 |
| [D-Pen$^2$, L-Cys$^5$, Thr$^6$]Enkephalin | 228 ± 52 | 0.60 ± 0.06 | 380 |
| [D-Cys$^2$, L-Pen$^5$] Enkephalin | 39.9 ± 1.5 | 0.75 ± 0.05 | 53.2 |
| [D-Cys$^2$, D-Pen$^5$] Enkephalin | 66.7 ± 1.3 | 0.13 ± 0.06 | 513 |
| [D-Pen$^2$, L-Pen$^5$] Enkephalin | 2720 ± 50.1 | 2.50 ± 0.03 | 1088 |
| [D-Pen$^2$, D-Pen$^5$] Enkephalin | 6930 ± 124 | 2.19 ± 0.30 | 3164 |
| [D-Ala$^2$, D-Leu$^5$] Enkephalin | 24.3 ± 5.3 | 0.27 ± 0.06 | 90 |
| [D-Ala$^2$, Met$^5$] Enkephalinamide | 2.2 ± 0.4 | 3.75 ± 0.04 | 0.59 |
| Normorphine | 91 ± 19 | 540 ± 113 | 0.17 |

TABLE II

Cyclic Enkephalins - Rat Brain Binding Assays

| Analog | IC$_{50}$(nM) [$^3$H]NAL | [$^3$H]DADLE | IC$_{50}$(NAL)/ IC$_{50}$(DADLE) |
|---|---|---|---|
| [D-Pen$^2$, L-Cys$^5$] Enkephalinamide | 73.4 ± 15 | 3.35 ± 0.15 | 21.9 |
| [D-Pen$^2$, D-Cys$^5$] Enkephalinamide | 162 ± 35 | 7.20 ± 1.8 | 22.6 |
| [D-Pen$^2$, L-Cys$^5$] Enkephalin | 178 ± 16 | 11.7 ± 1.2 | 15.2 |
| [D-Pen$^2$, D-Cys$^5$] Enkephalin | 157 ± 74 | 26.0 ± 0.5 | 6.0 |
| [D-Pen$^2$, Cys$^5$, Thr$^6$]Enkephalin | 146.4 ± 25 | 5.2 ± 0.7 | 28.2 |
| [D-Cys$^2$, L-Pen$^5$] Enkephalin | 52.7 ± 2.3 | 5.4 ± 0.1 | 9.8 |
| [D-Cys$^2$, D-Pen$^5$] | 22.2 ± 2.8 | 3.5 ± 0.8 | 6.3 |

TABLE II-continued

Cyclic Enkephalins - Rat Brain Binding Assays

| Analog | IC$_{50}$(nM) [$^3$H]NAL | [$^3$H]DADLE | IC$_{50}$ (NAL)/ IC$_{50}$ (DADLE) |
|---|---|---|---|
| Enkephalin [D-Pen$^2$, L-Pen$^5$] | 3710 ± 740 | 10.0 ± 2.2 | 371 |
| Enkephalin [D-Pen$^2$, D-Pen$^5$] | 2840 ± 670 | 16.2 ± 0.9 | 175 |
| Enkephalin | | | |
| Morphine | 23.3 ± 2.4 | 27.2 ± 1.2 | 0.9 |
| [Leu$^5$]Enkephalin | 35.0 ± 1.9 | 1.15 ± 0.15 | 30.4 |
| [Met$^5$]Enkephalin | 27.0 ± 6.4 | 1.75 ± 0.05 | 15.4 |
| [D-Ser$^2$, Leu$^5$, Thr$^6$]Enkephalin | 88 ± 6 | 5.73 ± 0.42 | 15.4 |
| [D-Thr$^2$, Leu$^5$, Thr$^6$]Enkephalin | 36.3 ± 3.8 | 6.40 ± 0.60 | 5.7 |

In view of the positive results obtained with these tests, the claimed delta receptor agonist compounds are believed to be useful in the treatment of pain without the undesirable side effects associated with previously known opiates. Compounds according to the present invention having antagonist activity are believed to behave in a manner similar to naloxone and, thereby, are believed to be useful in those areas where narcotic antagonists have been useful in the prior art, including the treatment of Alzheimer's disease. See generally, Reisberg, B., Forris, S. H., Anand, R., Pervez, M., Giebel, V., and DeLoon, M. J., *New Eng. J. Med.*, vol. 308: 12, 721–722 (1983), which is specifically incorporated herein by reference.

Preparation of compounds within the scope of the present invention appear in the following examples.

EXAMPLE I

Preparation of
N$^\alpha$-tert-Butyloxycarbonyl-L-tyrosyl-S-benzyl-D-penicillaminyl-glycyl-L-phenylalanyl-S-p-methylbenzyl-L-cysteinyl-resin.

Chloromethylated (1.16 mmoles Cl/g resin) polystyrene resin crosslinked with 1% divinylbenzene (Lab Systems, Inc., San Mateo, CA) was used as the solid phase matrix. The carboxy terminal amino acid Boc-L-Cys(pMeBzl) was attached via an ester linkage using the procedure disclosed by Gisin, *Helv. Chim. Acta* 56, 1476 (1973), which is specifically incorporated herein by reference.

5.0 g of the above, dry Boc-L-Cys(S-pMeBzl)-resin, substituted to the extent of 0.2 mmoles amino acid/g resin was placed into a solid phase peptide synthesis reaction vessel and Boc-Phe-OH, Boc-Gly-OH, Boc-D-Pen(S-Bzl)-OH, and Boc-Tyr-OH were then incorporated onto the peptide resin sequentially according to the protocol listed in Agenda A yielding tert-Butyloxycarbonyl-L-tyrosyl-S-benzyl-D-penicillaminyl-glycyl-L-phenylalanyl-S-p-methylbenzyl-L-cysteinyl-resin.

AGENDA A

1. Wash for 2 min. with CH$_2$Cl$_2$ (repeat this step 4 times)
2. Treat with trifluoroacetic acid (hereinafter TFA)-CH$_2$Cl$_2$ Anisole (50:48:2, v/v) for 2 min.
3. Treat as in #2 for 20 min.
4. Wash for 2 min. with CH$_2$Cl$_2$ (repeat 3 times)
5. Treat with diisopropylethylamine (hereinafter DIEA)-CH$_2$Cl$_2$ (10:90 v/v) for 2 min. (repeat 2 times)
6. Wash for 2 min. with CH$_2$Cl$_2$ (repeat 4 times)
7. Ninhydrin test-Kaiser et al. *Anal. Biochem.* 34, 595 (1970), which is herein specifically incorporated by reference. If positive, proceed to step 8; if negative, repeat steps 3-7.
8. Treat with 3 equivalents of the appropriate Boc amino acid dissolved in CH$_2$Cl$_2$ or dimethylformamide (hereinafter DMF) and 2.4 equivalents each of dicyclohexylcarbodiimide (DCC) (in CH$_2$Cl$_2$) and 1-hydroxybenzotriazole (HOBt) (in DMF). Allow reaction to proceed for 1 to 3 hours.
9. Wash for 2 minutes with CH$_2$Cl$_2$ (3 times).
10. Wash for 2 minutes with EtOH (3 times).
11. Wash for 2 minutes with CH$_2$Cl$_2$ (4 times).
12. Ninhydrin test. If coupling is incomplete, repeat steps 8-12.

EXAMPLE II

Preparation of
L-Tyrosyl-D-penicillaminyl-glycyl-L-phenylalanyl-L-cysteinyl cyclic (2-5) disulfide 2.1 g of the protected peptide-resin from Example I was reacted with 20 ml anhydrous HF, 6 ml anisole, and 0.4 ml ethanedithiol at 0° C. for 1 hr. The mixture was evaporated in vacuo and the dried mixture of free peptide and resin was washed 3 times with 60 ml portions of ethyl acetate which was then discarded. The resin was then extracted 3 times with 60 ml portions of each of the following: 30% HOAc, 0.2N HOAc, and H$_2$O. The combined aqueous extracts were then lyophilized to a white powder. This powder, containing the free sulfhydryl form of the peptide, was dissolved in 1.2 liters of 0.1% HOAc which had been bubbled for 1 hour with nitrogen gas. The pH was raised to 8.5 with 3N NH$_4$OH and four-8 ml aliquots of 0.01N K$_3$Fe(CN)$_6$ solution were added to the stirring solution with several minutes being allowed between additions of K$_3$Fe(CN)$_6$ to observe the disappearance of the characteristic yellow color of the Fe(CN)$_6^{-3}$ ion. The point at which the yellow color persisted was noted and an additional volume of K$_3$Fe(CN)$_6$ solution, equivalent to the total required for a persistent yellow solution, was added. The oxidation was allowed to proceed for an additional 1-2 hrs. after which the pH was lowered to 5 with glacial acetic acid. Ten ml (settled volume) of Rexyn 203 (Cl$^-$ form) or AG3X4A (Cl$^-$ form) anion exchange resin was added and the solution stirred for 20 min. The mixture was then filtered, the anion exchange resin was washed 3 times with 50 ml 30% HOAc, and the solution volume was reduced to ca. 200 ml by rotary evaporation. The remaining solution was lyophilized to a cream colored solid.

The solid was dissolved in ca. 6 ml of the organic phase of 1-butanol-acetic acid-water (4:1:5 (v/v) partition system and partially purified by partition chromatography on Sephadex G-25 block polymerizate using this same partition system. The compound eluted with an R$_f$=0.52 yielding 50 mg of slightly impure product. The product was further purified by gel chromatography on Sephadex G-15 using 30% HOAc as eluant and yielded 35 mg of pure L-tyrosyl-D-penicillaminyl-glycyl-L-phenylalanyl-L-cysteinyl cyclic (2-5) disulfide. Amino Acid Analysis: Tyr 1.02, half Cys+half Pen 1.95, Gly 0.94, Phe 1.09; TLC $R_f$: 0.40 (BAW), 0.75 (BPAW), 0.23 (BW), 0.64 (APW), as used above, the following abbreviations for solvent systems have the following connotations: BAW refers to 1-butanol-acetic acid-water (4:1:5, upper phase only); BPAW refers to 1-butanol-pyridine-acetic acid-water (15:10:3:12); BW refers to 1-butanol-water (3.5% acetic acid, 1.5% pyridine) (upper phase only); and APW refers to amyl alcohol-pyridine-water (7:7:6).

EXAMPLE III

Preparation of L-Tyrosyl-D-penicillaminyl-glycyl-L-phenylalanyl-L-cysteinyl amide cyclic (2-5) disulfide A portion of the product of Example I was subjected to steps 1-7 of Agenda A to remove the tyrosyl $N^\alpha$Boc protecting group, filtered, and dried in vacuo. One hundred twenty-five ml of freshly distilled methanol was saturated with anhydrous $NH_3$ and approximately 4 g of the peptide resin was added. The reaction vessel was wired shut and the mixture was stirred at room temperature for four days. The ammonia was then removed by a vacuum and the solution evaporated to dryness. Sixty ml DMF was added to the resin and stirred at 55° C. for 18 hrs after which the resin was filtered, saving the DMF, and resuspended in an additional 60 ml of DMF and heated with stirring at 90° C. for 3 hrs. The solution was then filtered and the DMF fractions combined and the volume reduced by evaporation to ca. 5 ml. Water (50 ml) was added to the remaining DMF solution and the resulting mixture was lyophilized yielding 0.53 g of crude Tyr-D-Pen(S-Bzl)-Gly-Phe-L-Cys(S-pMeBzl)amide.

A 0.3 g portion of this protected pentapeptide was added to 300 ml liquid $NH_3$ which had been distilled from sodium and the solution was warmed to the boiling point. The solution was treated with sodium until a blue color persisted for 90 seconds after which enough $NH_4Cl$ was added to render the solution colorless. The volume of $NH_3$ was reduced to ca. 20 ml by a stream of $N_2$ gas and the remaining $NH_3$ removed by lyophilization. The resulting solid was dissolved in $N_2$ purged HOAc and the free sulfhydryls oxidized by treatment with $K_3Fe(CN)_6$ as in Example II. Purification was affected as in Example II yielding 66 mg of pure

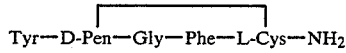

cyclic (2-5)disulfide. Amino Acid Analysis: Tyr 1.02, half Cys+half Pen 1.79, Gly 0.96, Phe 1.02; TLC $R_f$: 0.27 (CMA), 0.53 (BAW), 0.35 (BW), 0.85 (BPAW) CMA, chloroform-methanol-acetic acid (65:35:4).

EXAMPLE IV

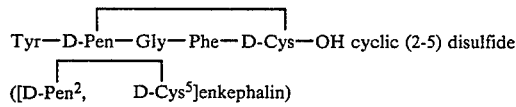

was prepared as in Examples I and II.

EXAMPLE V

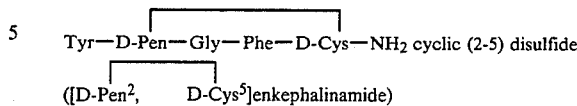

was prepared as in Examples I and III.

EXAMPLE VI

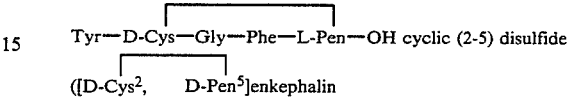

was prepared as in Examples I and II.

EXAMPLE VII

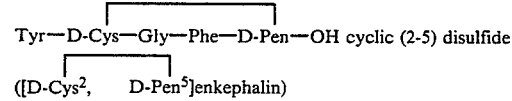

was prepared as in Examples I and II.

EXAMPLE VIII

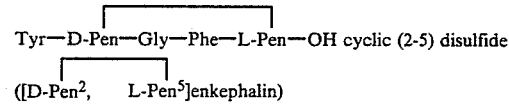

was prepared as in Examples I and II.

EXAMPLE IX

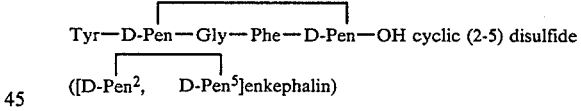

was prepared as in Examples I and II.

EXAMPLE X

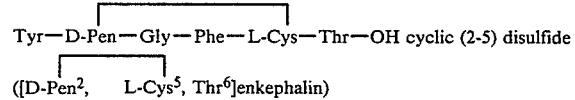

was prepared as in Examples I and II.

The compounds of Examples II-X were examined for their ability to inhibit electrically stimulated muscle contractions in the guinea pig ileum (GPI) assay and in the mouse vas deferens (MVD) assay. The GPI preparation has been shown to contain primarily mu type opiate receptors and the MVD preparation primarily delta type opiate receptors. Thus, comparisons of $IC_{50}$ values in these two assay systems, as shown in Table I, provide a measure of the receptor specificity of the tested analogs. The results shown in Table I clearly indicate the high delta receptor selectivity of these analogs, which in the case of Example IX is greater than 3100, i.e., about thirty-five times greater than that of [D-Ala$^2$, D-Leu$^5$]enkephalin, the prototypical delta selective ligand.

The compounds of Example II-X were also examined for their ability to displace the tritiated ligands, ([$^3$H]NAL), a highly mu receptor selective alkaloid opiate, and ([$^3$H]DADLE) from rat brain membrane preparations. As shown in Table II, the results indicate that the cyclic enkephalin analogs exhibit weak binding to mu receptors as determined by displacement of [$^3$H]naloxone and a higher affinity for delta receptors as measured by displacement of ([$^3$H]DADLE). Also listed in this table are the results for [D-Ser$^2$, Leu$^5$, Thr$^6$]enkephalin, (hereinafter sometimes referred to as "DSTLE") and [D-Thr$^2$, Leu$^5$, Thr$^6$]enkephalin, (hereinafter sometimes referred to as "DTTLE"), which have been reported to possess high delta receptor selectivity. See Gacel, G., Fournie-Zaluski, M. C., Roques, B. P., *F.E.B.S. Lett.* 118: 245–247 (1980), which is herein specifically incorporated by reference. As shown in Table II, the compounds of Examples II-X exhibit similar or (in the case of Examples VIII and IX) much greater delta receptor selectivities in these binding assays than do DSTLE and DTTLE.

The in vivo, in vitro, and receptor binding assays are described in detail below.

In Vivo Bioassays. Female Sprague Dawley rats (250-300 g) were anesthetized with ketamine HCl (100 mg/kg ip.) and polyethylene cannulas (PE. 10, Clay Adams, Parsipanny, N.Y.) were inserted in the right lateral cerebral ventricle (2 mm lateral, 2 mm posterior to bregma). A small stainless steel anchoring screw was threaded into the skull and the cannula was secured in place with a small mound of dental acrylic. The animals were housed individually and were allowed to recover for 72 hours. Drugs were dissolved in saline and intracerebral injections were administered in a volume of 5 μl. Analgesia was assessed by measuring the latency to rear paw lick when the animal was placed on a 55.5° C. hot plate 10, 20, 40, and 120 minutes following peptide treatment. A fifty second cut-off was used and animals not responding within this time period were considered analgesic. Some animals were pre-treated with naloxone (2 mg/kg ip.) ten minutes prior to peptide treatment.

In Vitro Bioassays. The guinea pig ileum longitudinal muscle-myenteric plexus preparation was prepared following the method of Kosterlitz et al. Agonists were added to the tissue bath and remained in contact with the tissue for a maximum of three minutes. Concentrations were randomized and were added at intervals of fifteen minutes, during which the tissue was washed several times. This procedure was used to avoid the development of acute tolerance.

The mouse vas deferens was prepared following the method of Hughes et al. One pair of vasa deferentia was used in each experiment. The buffer did not contain Mg$^{2+}$ ions and a similar dose cycle was used as in the GPI.

Inhibition of Opiate Receptor Binding. Brains from male Sprague-Dawley rats were rapidly removed following sacrifice. Whole brains with cerebellum removed were homogenized in 100 volumes of Tris-HCl buffer (pH 7.4 at 25° C.). Tissue homogenates were washed twice in the same buffer by centrifugation at 48,000×g for 10 min. Pellets were resuspended in the same buffer. Inhibition of opiate receptor binding was determined by incubating 100 l of brain homogenate (5% original wet w/v) with 1 nM of [$^3$H][D-Ala$^2$, D-Leu$^5$]enkephalin (31.3 Ci/mmol, New England Nuclear Inc.) and varying concentrations of either

[D-Pen$^2$, D-Cys$^5$]enkephalinamide,

[D-Pen$^2$, L-Cys$^5$]enkephalinamide,

[Leu$^5$]enkephalin, [Met$^5$]enkephalin, or morphine hydrochloride at 25° C. Total incubation volume was 2 ml. After 40 min., the mixture was rapidly filtered through Whatman GF/B glass fiber filters and washed 3 times with 5 ml of ice cold buffer. Minor modifications of this procedure were followed when [$^3$H]naloxone (37.7 Ci/mmol, New England Nuclear Inc.) was used to label opiate receptors. One hundred microliters of brain homogenate (2% original wet w/v) were incubated with 1.3 nM of [$^3$H]naloxone for 2 hours at 4° C. Filter bound radioactivity was quantitated by liquid scintillation spectrophotometry with an efficiency of 46%. Non-specific binding was defined as [$^3$H][D-Ala$^2$, D-Leu$^5$-]enkephalin or [$^3$H]naloxone bound in the presence of 1 μM leucine-enkephalin or 1 μM naltrexone, respectively.

It will be apparent to those skilled in the art that various modifications and variations can be made in the processes and products of the present invention. Thus, it is intended that the present invention cover the modifications and variations of this invention provided that they come within the scope of the appended claims and their equivalents.

What is claimed is:

1. A polypeptide of the formula:

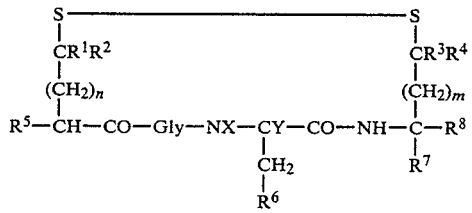

wherein

R$^1$ and R$^2$, which may be the same or different, are hydrogen, methyl, or a lower alkyl group having five or less carbon atoms;

R$^3$ and R$^4$, which may be the same or different, are hydrogen, methyl, or lower alkyl groups having five or less carbon atoms, provided, however, that R$^1$ and R$^2$, R$^3$ and R$^4$ may not all be hydrogen;

R$^5$ is hydrogen, L-tyrosine, D-tyrosine, or L-tyrosine or D-tyrosine substituted on the N$^\alpha$-amino with 1 or 2 lower alkyl or alkenyl groups;

R$^6$ is a substituted or unsubstituted aromatic radical;

RHU 7 is hydrogen or methyl;

R$^8$ is carboxylate, carboxamide or amino acid residue;

X and Y are hydrogen or methyl; and n and m, which may be the same or different, are 0 or 1.

2. A polypeptide according to claim 1 in which m and n are both zero.

3. A polypeptide according to claim 1 wherein either R$^1$ and R$^2$ are both methyl or R$^3$ and R$^4$ are both methyl.

4. A compound according to claim 1 wherein said polypeptide compound has the ability to bind to the delta receptor and, when bound to said delta receptor, has the ability to act as either an agonist or antagonist for said receptor.

5. A compound according to claim 4 wherein the compound is a delta receptor agonist.

6. A compound according to claim 5 wherein the compound is an analgesic.

7. A compound according to claim 5 wherein the compound is an analgesic and does not cross the placental barrier.

8. A compound according to claim 4 wherein the compound is a delta receptor antagonist.

9. A compound according to claim 4 wherein the compound is a delta receptor partial agonist.

10. A compound according to claim 4 wherein the compound is a delta receptor partial antagonist.

11. A polypeptide according to claim 1 which is a cyclized opioid compound wherein said cyclized portion of said opioid compound is conformationally restricted in a manner which enhances said compound's specificity for the delta opioid receptor.

12. A polypeptide according to claim 1 having the formula:

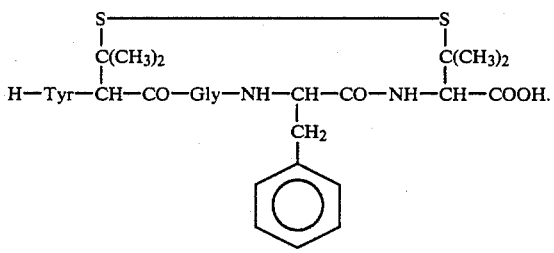

13. A polypeptide according to claim 1 wherein $R^6$ is selected from the group consisting of p-nitrophenyl, p-fluorophenyl, 1-naphthyl, p-aminophenyl, or 2-naphthyl.

14. A polypeptide according to claim 1, having the formula:

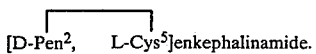
[D-Pen$^2$, L-Cys$^5$]enkephalinamide.

15. A polypeptide according to claim 1, having the formula:

[D-Pen$^2$, D-Cys$^5$]enkephalinamide.

16. A polypeptide according to claim 1, having the formula:

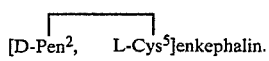
[D-Pen$^2$, L-Cys$^5$]enkephalin.

17. A polypeptide according to claim 1, having the formula:

[D-Pen$^2$, D-Cys$^5$]enkephalin.

18. A polypeptide according to claim 1, having the formula:

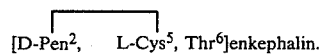
[D-Pen$^2$, L-Cys$^5$, Thr$^6$]enkephalin.

19. A polypeptide according to claim 1, having the formula:

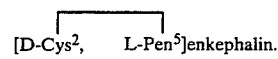
[D-Cys$^2$, L-Pen$^5$]enkephalin.

20. A polypeptide according to claim 1, having the formula:

[D-Cys$^2$, D-Pen$^5$]enkephalin.

21. A polypeptide according to claim 1, having the formula:

[D-Pen$^2$, L-Pen$^5$]enkephalin.

22. A process of inducing analgesia in humans and lower animals by administering a safe and effective amount of an opioid receptor agonist according to claim 5.

23. A pharmaceutical composition comprising an opioid receptor agonist having enhanced specificity for delta opioid receptors of the formula:

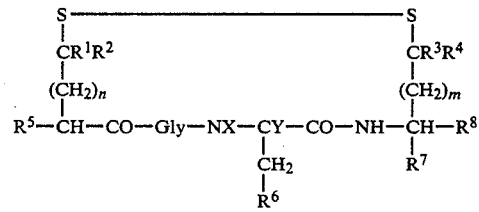

wherein
$R^1$ and $R^2$, which may be the same or different, are hydrogen, methyl, or a lower alkyl group having five or less carbon atoms;
$R^3$ and $R^4$, which may be the same or different, are hydrogen, methyl, or lower alkyl groups having five or less carbon atoms, provided, however, that $R^1$, $R^2$, $R^3$ and $R^4$ may not all be hydrogen;
$R^5$ is hydrogen, L-tryosine, D-tryosine, or D-tyrosine or L-tyrosine substituted on the $N^\alpha$-amino with 1 or 2 lower alkyl or alkenyl groups;
$R^6$ is a substituted or unsubstituted aromatic radical;
$R^7$ is hydrogen or methyl;
$R^8$ is carboxylate, carboxamide or amino acid residue;
X and Y are hydrogen or methyl; and
n and m, which may be the same or different, are 0 or 1,
or a pharmaceutically acceptable salt thereof, in a pharmaceutically acceptable carrier in a pharmaceutically acceptable amount.

24. A pharmaceutical composition comprising an opioid receptor agonist having enhanced specificity for delta opioid receptors of the formula:

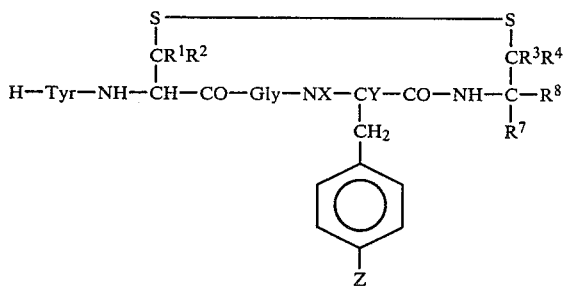

where:

$R^1$ and $R^2$, which may be the same or different, are hydrogen, methyl, or lower alkyl having one to five carbon atoms;

$R^3$ and $R^4$, which may be the same or different, are hydrogen, methyl, or lower alkyl having one to five carbon atoms, provided, however, that $R^1$, $R^2$, $R^3$, and $R^4$ may not al be hydrogen;

$R^7$ is hydrogen or methyl;

$R^8$ is carboxylate, carboxamide, or amino acid residue;

X and Y are hydrogen or methyl; and,

Z is hydrogen, nitro, fluoro, or amino, or a pharmaceutically acceptable salt thereof, in a pharmaceutically acceptable carrier, in a pharmaceutically acceptable amount.

25. A pharmaceutical composition according to claim 23 wherein said composition is an analgesic.

26. A pharmaceutical composition according to claim 24 wherein said composition is an analgesic.

* * * * *

UNITED STATES PATENT AND TRADEMARK OFFICE
CERTIFICATE OF CORRECTION

PATENT NO. : 4,518,711

DATED : May 21, 1985

INVENTOR(S) : Victor J. HRUBY and Henry MOSBERG

It is certified that error appears in the above-identified patent and that said Letters Patent is hereby corrected as shown below:

Claim 24, Col. 20, line 7, change "al" to --all--.

Signed and Sealed this

First Day of October 1985

[SEAL]

Attest:

Attesting Officer

DONALD J. QUIGG

Commissioner of Patents and Trademarks—Designate